United States Patent [19]

Amiot et al.

[11] Patent Number: 4,517,081

[45] Date of Patent: May 14, 1985

[54] DIALYZER REUSE MACHINE

[75] Inventors: Bruce P. Amiot, St. Louis Park; Larry E. Fuller, Minnetonka; Felix J. Martinez, Plymouth; Louis C. Cosentino, Wayzata; William H. Harm, Columbia Heights; Wayne I. Nelson, Brooklyn Park, all of Minn.

[73] Assignee: Renal Systems, Inc., Minneapolis, Minn.

[21] Appl. No.: 472,075

[22] Filed: Mar. 4, 1983

Related U.S. Application Data

[63] Continuation-in-part of Ser. No. 322,167, Nov. 17, 1981, abandoned.

[51] Int. Cl.³ .............................................. B01D 31/00
[52] U.S. Cl. ...................................... 210/85; 210/140; 210/321.3
[58] Field of Search ............... 417/185, 194; 210/96.2, 210/85, 87, 90, 140, 321.1, 321.3, 321.4, 321.2, 321.5

[56] References Cited

U.S. PATENT DOCUMENTS

| | | | |
|---|---|---|---|
| 1,017,792 | 2/1912 | O'Leary | 417/185 |
| 3,727,640 | 4/1973 | Sargeant | 417/194 X |
| 4,166,031 | 8/1979 | Hardy | 210/140 |
| 4,332,264 | 6/1982 | Gortz et al. | 134/57 R |

OTHER PUBLICATIONS

Kent's Mechanical Engineers Handbook, 12th Edition, 1950, pp. 5-79 through 5-83.
Pump Handbook, Karrassik, Krtuzsch, Frazer and Messina, Eds., pp. 4-1 through 4-19, McGraw-Hill (1976).
"How Clean is Clean?", United Medical Products, Inc. (undated brochure), 7 pp.
"Multiple Use of Dialyzers is Now a Practical Reality", United Medical Products Inc (undated brochure), 6 pp.
Cobe Dia-Kleen OX-3 (coil) Product Brochure (undated), 3 pp.
"Instruction Manual for MA-DE A100 Automatic Re-Use Machine and Cartridge", MA-DE, Inc., (1974), 9 pp.

*Primary Examiner*—Frank Spear
*Attorney, Agent, or Firm*—Schroeder, Siegfried Vidas & Arrett

[57] ABSTRACT

A dialyzer reuse machine comprising means for passing a series of liquid and gaseous fluids through the dialysate and blood compartments of the dialyzer at different flow rates according to a predetermined sequence for cleaning and disinfecting the dialyzer and means for accurately measuring the volume of the blood compartment upon completion of the dialyzer cleaning steps. Capacitive probe and load cell embodiments of the volume measuring means are disclosed. A specially designed jet pump permits a pressure leak test and dilution of stock chemicals to be performed using only tap water pressure as a source of motive force.

16 Claims, 9 Drawing Figures

DIALYZER REUSE MACHINE

This application is a continuation-in-part of U.S. application Ser. No. 322,167 filed Nov. 17, 1981, now abandoned.

BACKGROUND OF THE INVENTION

Hemodialysis using disposable dialyzers has become an extensively used method for the treatment of persons with kidney dysfunction or failure. Hollow fiber dialyzers having a blood compartment composed of a bundle of hollow fibers and a dialysate compartment formed by a sleeve surrounding the fiber bundle are a very widely used dialyzer of this type. While hemodialysis treatment has resulted in an improvement and in the prolongation of life, it is plagued with extremely high cost. As one method of reducing this cost, research has been performed which concluded that disposable hollow fiber dialyzers may be reused if they are adequately cleansed of bacterial, protein and other particulate matter. The cleaned dialyzer must be tested for sufficient dialyzing capability (the hollow fibers eventually become plugged) and for leakage between the blood and dialysate compartment caused by broken fibers or broken seals.

Several machines for cleaning dialyzers have been developed, one of which includes testing means for testing leakage and dialyzing capability. The dialyzing capability test involves an evaluation of the ultrafiltration capability of the cleaned dialyzer.

It has been reported that ultrafiltration is not a reliable measurement of the dialyzing capability of cleansed dialyzers. The measured ultrafiltration capability may remain high while the dialyzer loses its ability to transfer important solutes of low and middle molecular weight. Measurement of the volume of the dialyzer blood compartment ie., the internal volume of the blood compartment fiber bundle, has been shown to provide a much more reliable indicator of the dialyzing capability of a hollow fiber dialyzer than ultrafiltration measurement techniques. The fiber bundle volume is related directly to the surface area of the blood compartment—the principal factor affecting the mass transfer capability of the dialyzer. Furthermore, even with new dialyzers, the dialyzer blood compartment volume is manufactured to a closer specification than is ultrafiltration capability. To date, however, no automatic means for measuring the blood compartment volume of a cleansed dialyzer has been developed.

BRIEF DESCRIPTION OF THE INVENTION

The present invention relates to an alternative dialyzer reuse machine which utilizes an automatic measurement of the dialyzer blood compartment volume as an indicator of dialyzing capability rather than the previously used ultrafiltration performance test. In its broadest aspect, the inventive machine comprises means for passing a series of liquid and gaseous fluids through the dialysate and blood compartments of the dialyzer at different flow rates according to a predetermined sequence for cleaning and disinfecting the dialyzer, and means for accurately measuring the volume of the blood compartment upon completion of the dialyzer cleaning steps.

The inventive machine is designed so that reasonable water tap pressures (as low as about 30 lbs/sq. in.) may be used to move the fluids through the machine and the dialyzer. Jet pump means powered by water at or below tap pressure serves as a motive means for moving fluids other than water through the machine and the dialyzer. The jet pump also permits the evacuation of one compartment of the dialyzer while the other compartment is left open to the atmosphere so that a pressure leak test may be performed by monitoring a loss of negative pressure in the evacuated compartment over time.

A further aspect of the inventive machine is a special tank means with liquid level measuring means combined therewith. The tank has a predetermined relationship between volume and liquid level in the tank so that a dialzyer blood compartment volume measurement may be obtained by filling the dialyzer blood compartment with water, drawing the water from the dialyzer blood compartment to the tank, measuring the liquid level in the tank (or the change in liquid level) and calculating the blood compartment volume in accordance with the known relationship between the tank level and volume. The calculation may conveniently be automatically performed by the electronic circuitry associated with the inventive machine. The tank may also be used for accomplishing dilutions of cleaning chemicals from commercially available stock solutions so that the risk of improper dilution and the hazard to technicians created by the handling of chemicals can be minimized.

An alternative tank means may be mounted on a calibrated load cell with associated circuitry converting the measured weight of water in the tank into an equivalent volume.

Electronic control means open and close a series of valves within the machine according to predetermined sequences and in response to liquid level or pressure measurements to cause the various fluids to move through the machine and dialyzer compartments for cleaning, testing and disinfecting the dialyzer and for sanitizing the machine after use.

DETAILED DESCRIPTION OF THE INVENTION

Figure 1:
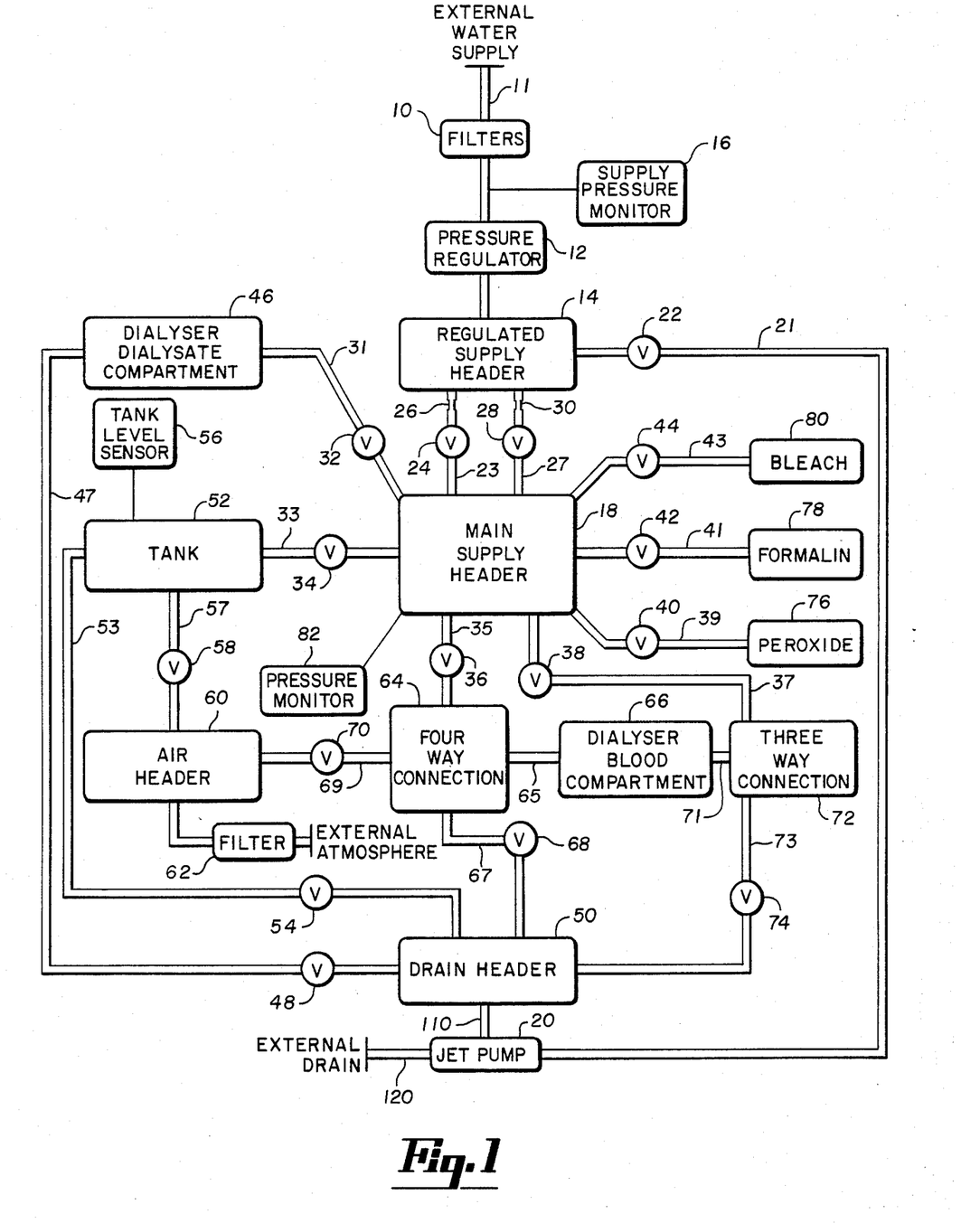
FIG. 1 is a schematic of the inventive machine.

FIG. 1 shows a schematic of the invention in its preferred embodiment. Water from an external water supply 11 is first passed through filter means 10 to remove particulate matter. The filtered water is then passed through a pressure regulator 12 providing a constant pressure feed to regulated supply header 14. A supply pressure monitor 16, connected to the electronic control means, not shown, may be provided to assure that adequate pressure is supplied by the external feed line to operate the machine. The supply monitor 16 may be located, as shown, before pressure regulator 12. Alternatively, monitor 16 may be located so as to monitor the pressure at regulated supply header 14. In either case, the electronic control means will preferably be programmed so as to prevent operation of the machine when supply pressure is inadequate.

Conduit means 21 connects the regulated supply header 14 to the jet pump 20. A valve means 22 in conduit 21 provides interruption of flow between header 14 and jet pump 20. Alternatively, the jet pump may be connected directly to the external water supply.

As shown in FIG. 1, the connection between regulated supply header 14 and main supply header 18 is provided by two routes. The first, conduit 23, includes valve 24 and flow limiting means such as fixed orifice 26. The second, conduit 27, includes valve 28 and flow limiting means such as fixed orifice 30. Orifices 26 and 30 are sized to provide high and low flow rates to the main supply header depending on which conduit route is utilized. Typically, a high flow rate would be about 6 liters per minute and a low flow rate about 0.5 liters per minute. The high flow rate is necessary for cleansing the dialyzer, particularly to dislodge protein matter in the hollow fibers of the dialyzer blood circuit. The low flow rate is desirable to provide accurate dilutions of cleansing chemicals as described hereinafter and to protect physical integrity of the dialyzer during the flow of water through the dialyzer dialysate compartment.

As an alternative to the dual connections between regulated supply header 14 and the main supply header 18 shown in FIG. 1, a single connection may be provided which includes a variable orifice valve which may be operated to provide high, low, or, if desired, intermediate flow rates.

In addition to conduits 23 and 27, the main supply header is connected to conduit means 31, 33, 35, 37, 39, 41 and 43 which include valves 32, 34, 36, 38, 40, 42, and 44, respectively for interrupting flow through the respective conduits.

Conduit 31 provides interruptable interconnection between header 18 and the dialysate compartment 46 of the dialyzer to be cleaned. The other end of the dialyzer dialysate compartment is connected by means of conduit 47, which includes valve 48, to a drain header 50. The end portions of conduits 31 and 47 which connect the dialysate compartment are preferably flexible tubing members which may be easily disconnected upon completion of the cleaning operation and reconnected to another dialyzer.

Conduit 33 provides interruptable interconnection between header 18 and tank 52. Tank 52 is also interruptedly connected to drain header 50 by conduit 53 and valve 54. Tank 52 includes a liquid level sensor 56 which permits volumes of fluid in the tank to be monitored. Tank 52 is also interruptedly connected by means of conduit 57 and valve 58 to air header 60 which provides communication with the external atmosphere. A filter 62 between air header 60 and the external atmosphere may optionally be included to prevent introduction of particulate contamination.

Conduit means 35, which includes valve 36, provides interruptable connection between the main header 18 and one arm of a four-way communication means 64. A conduit means 65, preferably a flexible tubing member, is connected to a second arm of the four-way communication means and to one end, preferably the arterial end, of the blood compartment 66 of the dialzyer to be cleaned. Another conduit 67, which includes valve 68 provides interruptable connection between four-way communication means 64 and the drain header 50. The fourth arm of communication means 64 is connected to a conduit 69, which includes valve 70 to provide interruptable connection between air header 60 and member 64.

Conduit 37 and valve 38 provide interruptable connection between the main supply header and a three way communication means 72. A second arm of communication means 72 connects with the venous end of the dialyzer blood compartment by means of flexible tubing conduit 71. Conduit 73 and valve 74 provide interruptable connection between drain header 50 and the third arm of communication means 72.

Conduits 39, 41, and 43 provide connection between the chemical supply sources 76, 78 and 80, respectively, and the main supply header. Valves 40, 42 and 44 provide means for interrupting such connections. As indicated in FIG. 1, these chemicals are preferably hydrogen peroxide (3%), formalin (37% formaldehyde solution) and bleach (5.25% sodium hypochlorite), all of which are commercially available standard solutions. Other chemicals or concentrations may be used, however, depending on the cleaning program adopted for the machine.

A pressure monitor 82 is also associated with the main supply header for monitoring pressure in the main supply header and leak testing the dialyzer.

The Tank

Essential to the present invention is a means for measuring the internal volume of the dialyzer blood compartment which comprises the fiber bundle, or bundles, and the blood distribution manifolds of the dialyzer which has been cleaned by the inventive machine. This measurement is performed by filling the dialyzer blood compartment completely with water, drawing the water from the dialyzer blood compartment into the tank and measuring the water volume obtained.

A variety of methods may be used to measure the volume of a liquid in a tank such as monitors for mass, pressure, or strain, float gauges, or a variety of ultrasonic and electromagnetic methods. The choice of method depends to a substantial degree on tank configuration, volume to be measured and sensitivity desired. In the inventive dialyzer reuse machine, it is desirable that the sensing method and tank configuration be chosen so as to allow accurate measurement of volumes of 0 to about 300 or 400 ml with about 5% accuracy or better. Furthermore, in the preferred embodiment of the invention, the reuse machine will also be capable of accurately producing approximately 1 liter of diluted cleansing chemicals from stock solutions.

Figure 2:
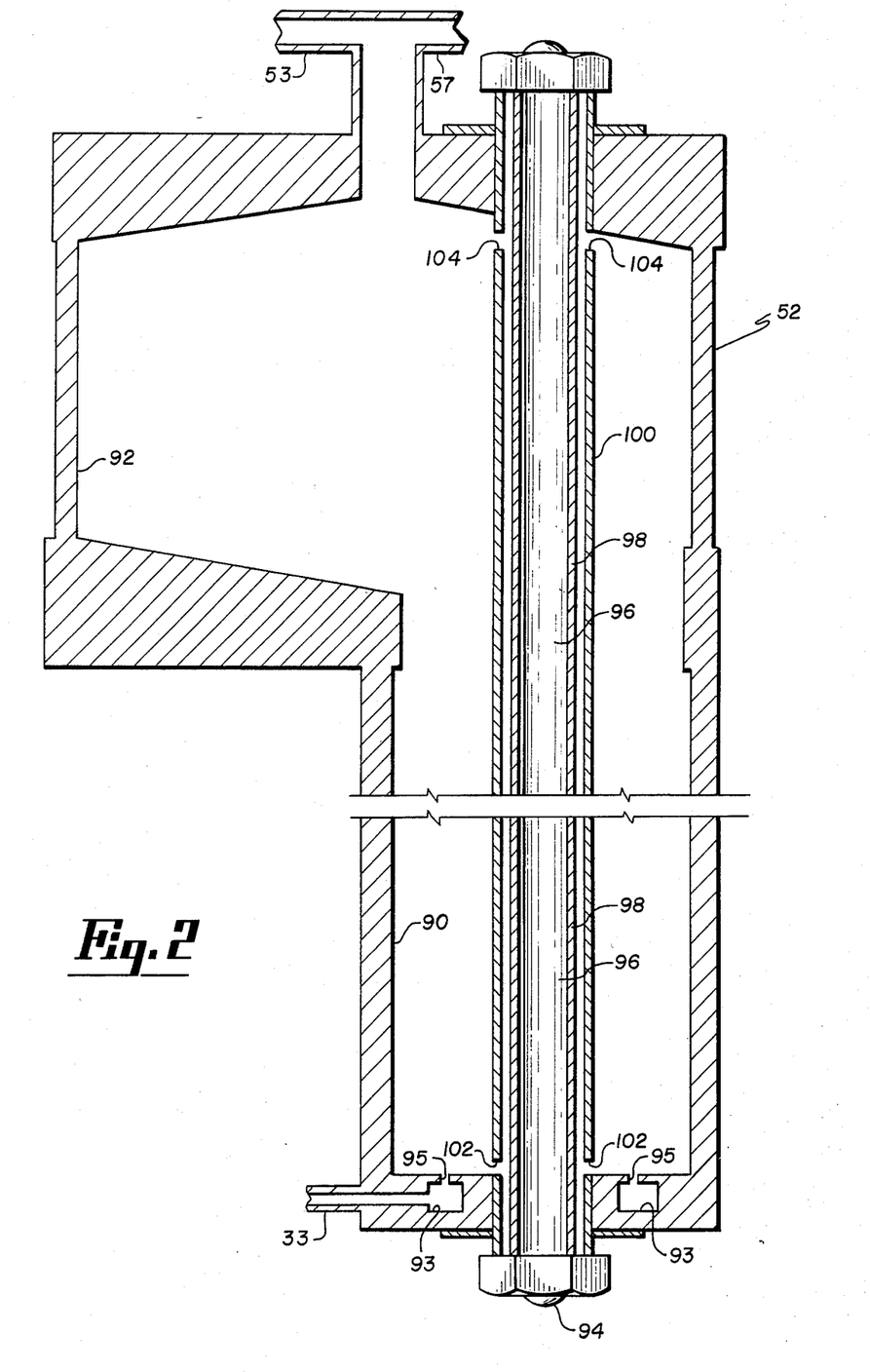
FIG. 2 is a side sectional view of the tank and capacitive probe of the inventive machine.

To accomplish both objectives, i.e., accurate blood compartment volume measurement and accurate dilution, a specialized tank design and capacitive probe combination may be used. The tank, generally designated by the numeral 52, is shown in FIG. 2. The tank contains a lower, higher resolution section 90 and an upper, high volume lower resolution section 92. Fluid communication between the tank and conduit means 33 is provided by circular gallery 93 in the bottom of the tank and holes 95 between the tank and gallery 93. This configuration permits the capacitance probe 94 to be utilized most efficiently. The capacitance probe 94 comprises a central core member 96 of a conductive material such as stainless steel which is coated with an insulating material 98 such as Teflon TM (polytetrafluoroethylene) or irradiated polyolefin. Insulated from, and surrounding core 96 is a tubular sheath or shell 100 also of a conductive material such as stainless steel. A thin uniform gap is left between the surface of coating 98 and shell 100. One or more ports 102 at the bottom of the probe permit liquid in the tank to enter and move up the probe in the space between the core and the outer shell. At the top of the probe, one or more ports 104 permit air to escape so that the liquid level in the probe gap equilibrates with the level of liquid in the body of the tank. For liquids of high dielectric constants such as water, the capacitance of the probe will change substantially as the liquid rises and thus a voltage change may be measured which corresponds to the level of the liquid in the tank.

Figure 3:
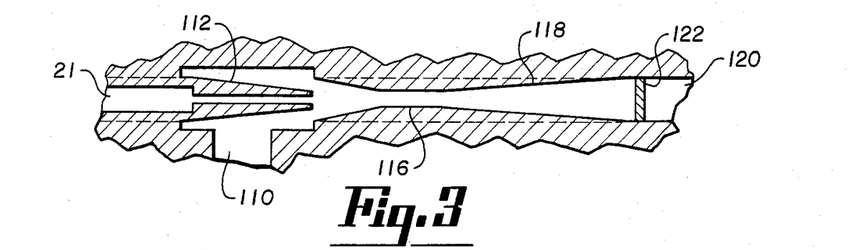
FIG. 3 is a side sectional view of the jet pump of the inventive machine.

By utilizing the configuration shown in FIG. 3 i.e., having a lower volume lower region and a higher volume upper region, the tank and probe can be used both for higher resolution measurements of dialyzer blood compartment volume and also for lower resolution, higher volume, dilution operations. The lower section results in a much higher volume change per height unit than is achieved at the upper region 92. Consequently, a higher sensitivity may be obtained from the probe in the lower region 90. This is important because the capacitance probe is required to resolve very small changes in tank volume (some dialyzers have a blood compartment volume of only about 50 cc).

As an example, a tank may be provided with a lower section 90 which contains about 74 cc per inch and is about 6 inches high, a total tank height to the 1 liter mark of about 8 inches, and a voltage ranging from 0 at 0 level to 10 volts at a 1 liter level. In such a tank, a resolution of 1 percent on a 70 cc dialyzer requires detection of a liquid level change of 0.0095 inches or about 0.0118 volts. This can be accomplished with a circuit sensitive to 1 picofarad, with a probe having a shell OD of about 0.84 inches, shell ID of about 0.72 inches, and an interior core OD of about 0.37 inches, including a coating of irradiated polyolefin about 0.011 inches thick.

Load Cell Embodiment

In some situations the capacitive probe discussed above may not give adequate performance. Significant instability in the electrical characteristics of stainless steel probes has been observed on occasion. This may be caused by the repeated alternate exposures to basic bleach and acidic formalin solutions. If reverse osmosis water is not used, a scale may be formed on the probe which changes its electrical characteristics. Scaling has been observed with both hard and softened waters.

As an alternative to the capacitive probe, a load cell may be used to measure the liquid volume within the tank. When water over a typical temperature range of between 15° and 41° C. is used in the tank, water density variations will be less than 1% and a direct correspondence between tank weight and water volume can be made.

Figure 8:
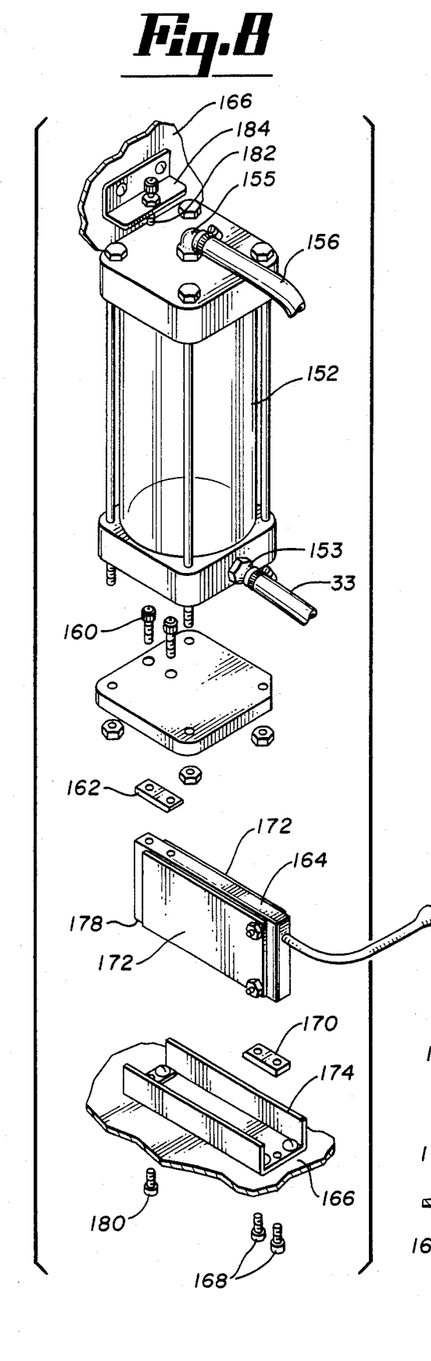
FIG. 8 is a pictorial exploded view of an alternative tank and load cell combination.
Figure 9:
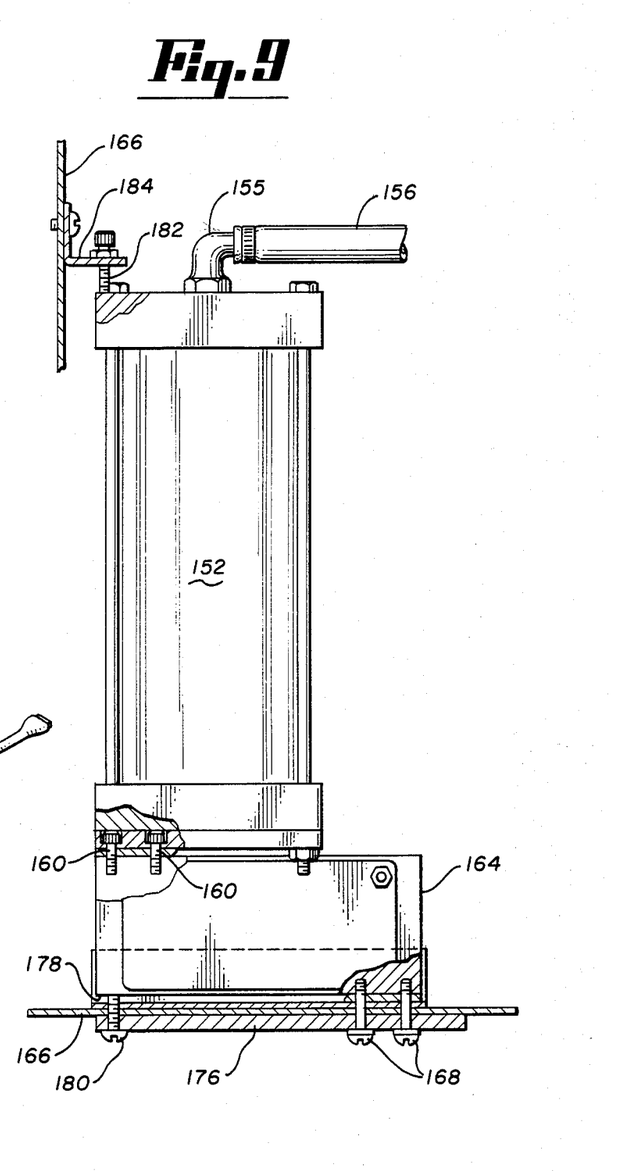
FIG. 9 is a side elevational view with parts cut away of the alternative tank and load cell combination of FIG. 8.

In the embodiment of FIGS. 8 and 9, a generally cylindrical tank 152 replaces tank 52 of the previous embodiment. Tank 152 includes a lower port 153 connecting to hose conduit 33 and an upper port 155 which is connected to conduits 53 and 57 of FIG. 1 by means of hose 156. Tank 152 should have a total volume capacity in excess of 1 liter, preferably about 1300–1400 ml.

Tank 152 is mounted by means of a pair of screws 160 and a spacer 162 to one end of load cell 164. The opposite diagonal end of 164 is mounted on the machine frame 166 by means of screws 168 and spacer 170. Load cell 164 is a commercial cell which includes a plurality of strain gauges which provide a variable electrical output, depending on the distortion to the frame caused by a weight change which is sensed by the strain gauges. Load cell 164 may be a commercial load cell, preferably a four gauge device having a 0–5 lb linear capacity with a maximum output of 2 mV/V±10% and a linear repeatability of 0.1%. A pair of shields 172 are preferably mounted on the side surfaces of the cell to protect the gauges from inadvertent contact with water or other chemicals which may occasionally leak from tank 152 or other points in the fluid conduit system.

Since the load cell senses the stress on the cell frame as a weight change, it is important that the machine frame 166 be sufficiently rigid to support the tank and cell assembly without flexing. To assure sufficient rigidity, stiffening means are preferably secured to the frame. Sufficient rigidity may be provided by channel bar 174 and aluminum plate 176 as shown in FIGS. 8 and 9.

In operation, the lower corner 178 of the load cell must be free to float. However, because excessive strain can cause the cell to change its output characteristics and permanently damage a load cell, it is important that the tank and cell be locked down during shipping or other movement so as to prevent excessive stress on the cell. The cell and tank are locked down by means of removable screws 180 and 182. Screw 180 passes through frame 166 to contact the lower floating corner 178 of the load cell. Screw 182 passes through bracket 184 mounted on frame 166 to contact the upper surface of tank 152. Both screws are removed prior to operation of the machine.

The load cell is calibrated so that a change in tank weight can be read out as a corresponding water volume when testing dialyzer capacity. The control means is also preferably programmed to recognize predetermined tank masses to accomplish the desired dilutions of stock chemicals.

Jet Pump

A special feature of the present invention is the use of a jet pump to move liquids through the machine. Water at or above a pressure of about 30 lbs is used as a pumping fluid to efficiently move both water and air, a capability which is not available with known jet pump designs.

FIG. 3 shows a jet pump design for use with both aqueous liquids and air. Conduit means 21 provides water at a relatively high pressure to a nozzle 112 which increases the pumping fluid velocity. Conduit 110 connects a drain header 50, providing an inlet for the pumped fluid. The pumped fluid is entrained by the water injected through nozzle 112 before or as both fluids pass through throat 116 and tapered diffuser section 118 to the external drain outlet 120.

Because the jet pump is designed to pump both liquid and air, certain design modifications are necessary from typical jet pump designs which only pump one kind of fluid. Liquid pumps require a much larger throat region than do pumps moving air in order to operate efficiently. To accommodate liquid pumping, the throat region must be designed accordingly. Additionally, the throat must not present substantial resistance to liquid flowing from the drain header to the external drain when the pumping fluid is not flowing. However, at the pumping fluid supply pressures utilized, the jet from the nozzle remains compact when attempting to pump air and the pump will not function with any practical efficiency. Therefore, to permit pumping of both air and water, a flow interrupter member such as thin rod 122 is placed in the discharge to break up the jet, flooding the sides of the diffuser section and forcing air pumping to start. Although the flow interrupter may take a variety of configurations, it is desirable that its size be small and its placement be beyond the tapered discharge region 118 so as to minimize the flow resistance it creates. Actual location of the flow interrupter will be determined empirically for a given system since effective placement is dependent upon pumping fluid flow rate and conduit cross-sectional area.

Vortex Suppression

Figures 4, 5, 6, 7:
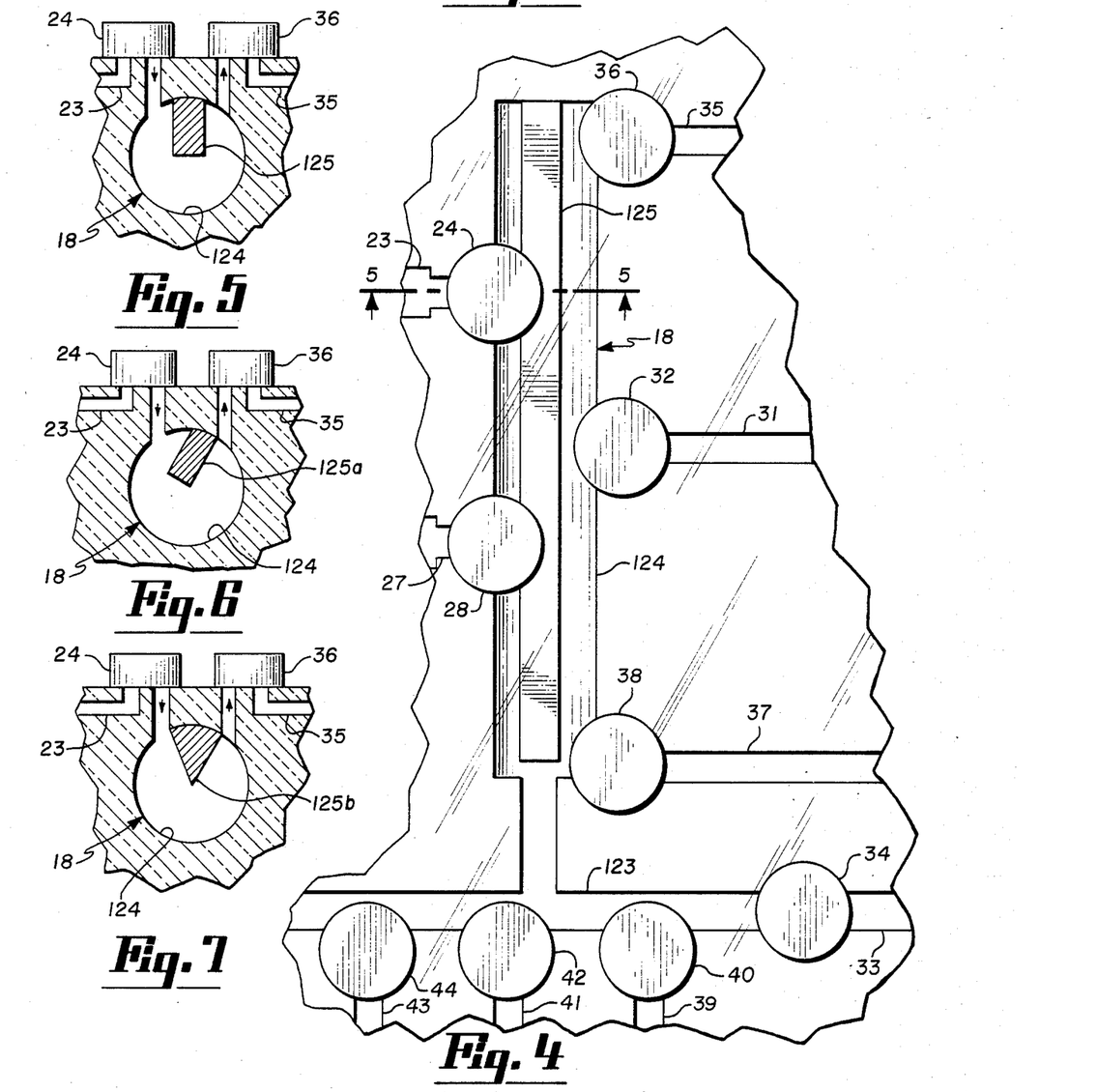
FIG. 4 is a top plan view of the main supply header portion of a transparent manifold for the inventive machine.
FIG. 5 is a side sectional view taken along line 5—5 of FIG. 4 showing a vortex suppression blade.
FIG. 6 is a view as in FIG. 5 with an alternate vortex suppression blade.
FIG. 7 is a view as in FIGS. 5 and 6 with a preferred alternate vortex suppression blade configuration.

Because removal of protein or other deposited materials from the dialyzer requires high flow rates and the machine is designed to operate on typical tap water pressures, it is important that energy losses caused by vortices or whirlpools in the pipes and/or manifold galleries of the present machine be minimized. FIG. 4 shows a configuration of a main supply header 18, including subsections 123 and 124. Main supply header 18 utilizes a vortex interrupter and flow director in the larger section 124 into which the high flow water conduit means 23 feeds, to minimize energy losses caused by tangential feeding of high velocity water. By making the main supply header large relative to the manifold galleries or conduits leading thereto and by placing a blade 125 within portion 124 of the header between the water inlet and principle water outlet conduits, the blade extending from the header wall to near the center thereof, the vortex will be interrupted and flow directed to the outlet ports minimizing energy losses.

FIGS. 5–7 show sectional views of subsection 124 of the main supply header 18 with several alternate blade configurations. A straight blade 125 as shown in FIG. 5, merely interrupts vortex flow. The angled blade 125a of FIG. 6 suppresses vortices and directs flow. The solid V-shaped blade 125b of FIG. 7 is a preferred configuration. Other configurations may be used with varying degrees of success including blades which do not contact the upper edge of the header and blades which extend all the way through the header and include a plurality of ports therethrough.

Operation of the Machine

An example program for cleaning and testing a dialyzer with the capacitive probe embodiment of the inventive machine follows. The same program can be used with the load cell embodiment by responding to sensed tank weight rather than liquid level. All valves are closed in the de-energized state and, if not stated otherwise valves are closed between each numbered step.

1. Rinse and Drain tank.
    Energize valves 24, 34, and 54.
    De-energize valves when the tank level reaches predetermined point near tank full level.
    Energize valves 28, 34, and 54.
    De-energize valves when the tank level reaches full level.
    Energize valves 22, 38, 74, 34, and 58.
    De-energize valves when tank level reaches zero.
2. Fill and flush dialysate compartment.
    Energize valves 28, 36, 32 and 48.
    (Opening valve 36 equalizes the pressure on both sides of the hollow fibers of the blood compartment to protect the fibers).
3. Flush fibers from arterial to venous.
    Energize valves 24, 36, and 74.
4. Draw concentrated peroxide into tank.
    Energize valves 22, 34, 54 and 40.
    De-energize valves when liquid level reaches predetermined point.
5. Dilute peroxide.
    Energize valves 24, 34, and 54.
    De-energize valves when tank level reaches predetermined point near final dilution.
    Energize valves 28, 34 and 54.
    De-energize valves when tank level reaches final dilution point.
6. Draw peroxide to dialysate compartment.
    Energize valves 22, 68, 74, 32, 48, 34 and 58.
    De-energize valves when tank level reaches zero.
7. Hold peroxide in dialysate compartment.
    Energize valves 68 and 74.
8. Rinse dialysate compartment.
    Energize valves 28, 38, 32 and 48.
9. Flush fibers from arterial to venous.
    Energize valves 24, 36 and 74.
10. Flush fibers from venous to arterial.
    Energize valves 24, 68 and 38.

Test Dialyzer Volume

11. Drain fluid from fibers to tank.
Energize valves 22, 38, 48, 70, 34, and 54.
12. Hold volume and vent tank.
    Energize valve 58.
13. Measure tank level.
    Compare reference and measured levels, (reference volume is programmed into control electronics to be a given percentage, typically 90%, of the dialyzer manufacturer's specification for volume of new dialyzers.)
    If reference level is less than or equal to measured level, proceed to step 14. If reference level is greater than measured level, failure signals should be energized.
14. Drain Main Supply Header.
    Energize valves 22, 36, 38, 74 and 70. Test dialyzer for leaks.

Pressure Test Dialyzer

15. Drain dialysate compartment.
    Energize valves 22, 36, 32, 48 and 70.
16. Draw vacuum on dialysate compartment and supply header.
    Energize valves 22, 32, 48 and 70.
    De-energize valves when pressure reaches predetermined negative pressure (preferably about −250 mmHg).
17. Hold negative pressure.
    Energize valves 32 and 70.
    After test time (typically about 1 min.), proceed to next step unless pressure has increased to above failure limit (about −225 mmHg).
If pressure increases above failure limit before test period is over, failure signals should be energized.
18. Drain tank.
    Energize valves 22, 38, 74, 34 and 58.

De-energize valves when tank is empty.
19. Flood Supply Header.
   Energize valves 24, 36 and 68.
20. Refill dialysate compartment.
   Energize valves 28, 36, 32 and 48.

Disinfect Dialyzer

21. Flush dialyzer from venous to arterial.
   Energize valves 24, 68 and 38.
22. Drain tank.
   Energize valves 22, 36, 68, 34 and 58.
   De-energize valves when tank is empty.
23. Draw formalin into tank.
   Energize valves 22, 34, 54, and 42.
   De-energize valves when level in tank reaches pre-determined level.
24. Dilute formalin.
   Energize valves 24, 34 and 54.
   De-energize valves at predetermined tank level near final dilution level.
   Energize valves 28, 34 and 54.
   De-energize valves when tank level reaches desired dilution level.
25. Draw formalin to blood compartment.
   Energize valves 22, 68, 38, 48, 34 and 58.
   De-energize valves when tank is empty.
26. Depressurize system.
   Energize valves 36, 68, 48, 70, and 58.
   Disconnect and cap dialyzer.

When the dialyzer reuse machine is not to be used for a period of time, the machine should be sanitized. The dialysate compartment connections, conduits 31 and 47, are shunted as are the blood compartment connetions, conduits 65 and 71. A bleach solution is then passed through the machine. It is preferable that the machine contain a interlock device so that the sanitizing cycle can only be performed when the dialyzer connections are shunted, not when a dialyzer is connected. An example sanitize program follows:

1. Flood supply header with water.
   Energize valve 24, 36 and 74.
2. Flood dialysate circuit with water.
   Energize valves 24, 32 and 48.
3. Flood blood circuit with water.
   Energize valves 24, 68 and 38.
4. Empty tank.
   Energize valves 22, 38, 74, 34 and 58.
   De-energize valves when tank level reaches zero.
5. Draw concentrated bleach (5.25%) into tank.
   Energize valves 22, 34, 54, and 44.
   De-energize valves when level reaches predetermined point.
6. Dilute bleach.
   Energize valves 24, 34, and 54.
   De-energize valves when tank level reaches predetermined point near final dilution.
   Energize valves 28, 34 and 54.
   De-energize valves when tank level reaches final dilution point.
7. Flood supply header with bleach.
   Energize valves 22, 36, 68, 34 and 58.
   De-energize valves to a tank level sufficient to assure that supply header has been flooded.
8. Flood dialysate circuit with bleach.
   Energize valves 22, 32, 48, 34 and 58.
   De-energize valves when the tank reaches a level sufficient to assure that the dialysate circuit has been flooded.
9. Flood blood circuit with bleach.
   Energize valves 22, 68, 38, 34 and 58.
   De-energize valves when tank level reaches zero.
10. Draw concentrated bleach into tank.
    Energize valves 22, 34, 54 and 44.
    De-energize valves when level reaches predetermined point.
11. Dilute bleach.
    Energize valves 24, 34 and 54.
    De-energize valves when tank level reaches predetermined intermediate point.
    Energize valves 28, 34 and 54.
    De-energize valves when tank is full.
12. Hold system in bleach typically about 20 minutes.
13. Drain tank.
    Energize valves 22, 36, 68, 34 and 58.
    De-energize valves when tank level reaches zero.
14. Tank purge.
    Energize valves 22, 36, 68, 34 and 58.
15. Drain supply header.
    Energize valves 22, 36, 68, 38, 74 and 70.
16. Fill tank with rinse water.
    Energize valves 24, 34, and 54.
    Allow tank to flood.
17. Rinse blood circuit from arterial to venous.
    Energize valves 24, 36 and 74.
18. Rinse blood circuit from venous to arterial.
    Energize valves 24, 68 and 38.
19. Rinse dialysate circuit.
    Energize valves 24, 32 and 48.
20. Drain tank.
    Energize valves 22, 38, 74, 34 and 58.
    De-energize when tank is empty.
21. Drain supply header.
    Energize valves 22, 36, 38, 74 and 70.
22. Drain blood circuit.
    Energize valves 22, 74 and 70.
23. Drain dialysate circuit.
    Energize valves 22, 36, 32, 48 and 70.
24. End of sanitize cycle.

In a machine program as given above, chemical concentrations after dilutions will preferably be about 0.5% hydrogen peroxide solution, 5% formaldehyde solution and about 1% sodium hypochlorite.

As described above, pressure monitor 82 is used to test for leaks in the dialyzer. Monitor 82 is preferably associated with the main supply header 18 but may alternatively be associated with tank means 52 or 152, or on the dialysate circuit in conduits 31 or 47 between valves 32 and 48.

It should be understood that the invention is not limited to the preferred embodiments described above. Additionally, it should be understood that the machine of the invention can be used to purify other kinds of hollow filter blood purification devices, such as hemofilters, and that the claims are intended to cover the machine regardless of the actual devices cleansed therewith. Many further variations in machine structure and fluid flow program may be made without departing from the basic invention which is set forth in its various aspects in the following appended claims.

What is claimed is:

1. A machine for cleaning a used hemodialyzer, the dialyzer having a blood compartment and a dialysate compartment, the machine comprising:
   means for passing a series of liquid and gaseous fluids through the dialysate and blood compartments of the dialyzer at different flow rates according to a predetermined sequence, whereby the dialyzer may be cleansed, and means for accurately measuring the volume of the blood compartment upon completion of the cleansing of the dialyzer.

2. A machine as in claim 1 further including a jet pump as a motive means for moving said fluids through said machine and dialyzer, said pump powered by water at or below tap pressure as a pumping fluid and including a throat region of sufficient diameter to permit both pumping of water thereby and draining of water therethrough, said pump further including a flow interrupter in the discharge region thereof to break the stream of pumping water so that air may also be pumped as desired.

3. A machine as in claim 1 wherein said fluid passing means includes water supply means; air supply means; cleaning fluid supply means; tank means; conduit means for interruptably interconnecting said dialyzer compartments, tank means and supply means; and control means for moving said water, air or cleaning fluids through said tank and dialyzer according to a predetermined sequence, and wherein said tank means includes liquid volume measuring means associated therewith.

4. A machine as in claim 3 wherein said tank includes a region having a predetermined relationship between liquid level and volume and wherein said volume measuring means includes means for accurately sensing the liquid level within the tank and means for converting said sensed level to a corresponding volume measurement.

5. A machine as in claim 4 wherein said means for accurately sensing liquid level within the tank is a capacitive probe.

6. A machine as in claim 5 where the tank means includes a lower region, and an upper region, said lower region having a relatively lower increase in volume per unit increase in liquid level than said upper region, and said capacitive probe extending through both the upper and lower regions of the tank.

7. A machine as in claim 6 wherein said means for drawing said predetermined partial vacuum on the dialyzer compartment is a jet pump powered by water at or below tap pressure.

8. A machine as in claim 3 wherein said liquid volume measuring means includes a load cell having said tank operatably mounted thereon whereby a change in tank weight may be sensed by said load cell, and means for connecting said sensed tank weight change to a corresponding volume of liquid within the tank.

9. A machine as in claim 3 wherein the predetermined sequence for moving fluids through the tank and dialyzer compartment includes at least one automatic dilution of a stock for cleaning or sterilizing fluid within the tank before passing said fluid into a dialyzer compartment.

10. A machine as in claim 1 further including means for drawing a predetermined partial vacuum on one of said dialyzer compartments with the other dialyzer compartment open to the atmosphere, and means for measuring the pressure change over time in the evacuated compartment, whereby leaks between the dialyzer blood and dialysate compartments may be detected.

11. A machine for cleansing and disinfecting a hemodialyzer device so that it may be reused, the dialyzer device including a dialysate compartment and a blood compartment and each said compartment communicating with an inlet port and an outlet port, the machine comprising:

a regulated supply header;
a supply header;
tank means;
an air header open to the atmosphere;
a drain header;
jet pump means including a pump fluid inlet, a pump fluid inlet and a discharge outlet open to the atmosphere;
means for supplying water of regulated pressure to the regulated supply header;
a four-way fluid communication means;
a three-way fluid communication means;
first conduit means for supplying water at or above about 30 lbs pressure to said jet pump pumping fluid inlet;
second conduit means extending between said main supply header and said tank;
third conduit means extending between said main supply header and one branch of said four-way conduit union;
fourth conduit means extending between said main supply header and one branch of said three-way communication means;
fifth conduit means extending between a second branch of said four-way communication and said drain header;
sixth conduit means extending between a second branch of said three-way communication means and said drain header;
seventh conduit means extending between said tank and said drain header;
eighth conduit means extending between said tank and said air header;
ninth conduit means extending between a third branch of said four-way communication means and said air header;
tenth conduit means for removably connecting said main supply header to one port of said dialyzer dialysate compartment;
eleventh conduit means for removably connecting said drain header to the other port of said dialyzer dialysate compartment;
twelfth conduit means for removably connecting the fourth branch of said four-way communication means to one port of the dialyzer blood compartment;
thirteenth conduit means for removably connecting the third arm of said three-way communication means to the other port of said dialyzer blood compartment;
fourteenth conduit means between said drain header and said jet pump fluid inlet;
said first through eleventh conduit means each including a valve means therein for interrupting fluid flow therethrough;
a plurality of chemical supply conduit means, each said chemical supply conduit means connected to said main supply header and including means for connecting a chemical supply source thereto and further including a control valve means therein for interrupting flow between said chemical supply source and said main supply header;
fifteenth conduit means between said regulated supply header and said main supply header, said fifteenth conduit means including variable flow supply means for interruptably supplying water at a plurality of flow rates to said main supply header; and, electronic control means for opening and closing said valve means and variable flow supply means according to predetermined sequences to pass fluids through the machine and dialyzer compartments for cleansing, testing and disinfecting the dialyzer, said electronic control means including means responsive to liquid volume within the tank for monitoring the liquid volume in the tank and initiating said predetermined sequences in response thereto.

12. A machine as in claim 11 wherein said electronic control means further includes pressure monitoring means for monitoring a negative pressure applied to one of said dialyzer compartments.

13. A machine as in claim 11 wherein the means responsive to liquid volume within the tank includes a capacitive probe within the tank producing an output indicative of liquid level.

14. A machine as in claim 11 wherein the means responsive to a liquid volume within the tank includes load cell means, said tank operably mounted thereon so that the load cell produces an output indicative of tank weight.

15. A machine as in claim 11 wherein said fifteenth conduit means includes a pair of conduit members, each said conduit member including a valve therein for interrupting flow therethrough and further including a fixed orifice means therein, one said orifice larger than the other, whereby high or low flow rate water may be supplied to said main supply header as desired.

16. A machine as in claim 11 wherein the electronic control means includes at least one predetermined sequence for automatically diluting a stock cleaning or sterilizing fluid within the tank before passing said fluid into a dialyzer compartment.

* * * * *